United States Patent [19]

Soe et al.

[11] Patent Number: 5,500,345
[45] Date of Patent: Mar. 19, 1996

[54] HYBRIDOMAS PRODUCING MONOCLONAL ANTIBODIES SPECIFIC FOR C-REACTIVE PROTEIN AND METHODS FOR DETECTION OF C-REACTIVE PROTEIN

[75] Inventors: Gilbu Soe, Inba; Isao Kohno, Funabashi; Michiyo Tanaka, Sakura, all of Japan

[73] Assignee: Iatron Laboratories, Inc., Tokyo, Japan

[21] Appl. No.: 357,540

[22] Filed: Dec. 16, 1994

Related U.S. Application Data

[63] Continuation of Ser. No. 117,632, Sep. 7, 1993, abandoned, which is a continuation of Ser. No. 635,616, Dec. 21, 1990, abandoned.

[30] Foreign Application Priority Data

Apr. 25, 1989 [JP] Japan ..................... 1-103471

[51] Int. Cl.[6] ........................... G01N 33/53; C12N 5/20; C07K 16/18
[52] U.S. Cl. .................. 435/7.1; 435/240.27; 435/70.21; 435/172.2; 530/388.2; 436/548
[58] Field of Search .................. 530/388.2; 435/240.27, 435/172.2, 70.21, 7.1; 436/548

[56] References Cited

FOREIGN PATENT DOCUMENTS

| | | |
|---|---|---|
| 62-36399 | 2/1987 | Japan . |
| 62-210984 | 9/1987 | Japan . |
| 62-210985 | 9/1987 | Japan . |
| 62-218866 | 9/1987 | Japan . |
| 8908261 | 8/1989 | WIPO . |

OTHER PUBLICATIONS

J. Tseng et al., Hybridoma, vol. 7, No. 2, 1988, pp. 185–191.
K. H. Roux et al. Journal of Immunology, vol. 131, No. 5, 1983, pp. 2411–2415.
Lyerly et al. J. Clin. Microbiol. 21: 12–14, 1985.
Rench et al. J. Clin Microbiol 20:852–854 1984.
Collet–Cassart et al. J. Immunol. Mtds 125: 137–141 1989.
Tanner et al. Clinical Chimica Acta 147: 267–272 1985.
Hirai et al. Protides of of the Biological Fluids 34: 283–286 1986.

Primary Examiner—Paula K. Hutzell
Attorney, Agent, or Firm—Michael N. Meller

[57] ABSTRACT

Monoclonal antibodies specifically reacting with the side face of a C-reactive protein (CRP), i.e., monoclonal antibodies specifically reacting with the side face of a disk-like subunit of a C-reactive protein (CRP), hybridoma producing the monoclonal antibody, and methods for the use thereof are disclosed.

4 Claims, 2 Drawing Sheets

HYBRIDOMAS PRODUCING MONOCLONAL ANTIBODIES SPECIFIC FOR C-REACTIVE PROTEIN AND METHODS FOR DETECTION OF C-REACTIVE PROTEIN This application is a continuation, of application Ser. No. 08/117,632, Sep. 7, 1993, now abandoned, which is a continuation of application Ser. No. 07/635,616 filed Dec. 21, 1990, now abandoned.

TECHNICAL FIELD

The present invention relates to novel monoclonal antibodies specifically reactive to C-reactive protein, hybridoma cells secreting the monoclonal antibody, and immunoassay methods using the monoclonal antibody.

BACKGROUND ART

C-reactive protein (abbreviated as CRP) is one kind of acute phase proteins, and although its blood level rapidly increases on inflammatory diseases or the like accompanying the disorganization, it is present in healthy human blood only in a trace amount (at most 1 μg/ml). Therefore, it is widely used for the diagnosis of purulent diseases, rheumatosis and the like. As shown in FIG. 1, the CRP is a pentamer comprising five disk-like subunits (molecular weight about 20,000), and two monoclonal antibodies to the CRP have been constructed (The Journal of Immunology, Vol. 131, 2411–2415m). These are a monoclonal antibody which specifically reacts with the circular upper face of a disk-like subunit (A-face in FIG. 1; sometimes simply designated "A-face"), but does not react with the circular lower face of the disk-like subunit (B-face in FIG. 1; sometimes simply designated "B-face"); and a monoclonal antibody which reacts with the circular lower face (B-face) of a disk-like subunit, but does not react with the circular upper face (A-face) of the disk-like subunit. Nevertheless, a binding of the former monoclonal antibody or the latter monoclonal antibody to an insoluble carrier, followed by mixing with a CRP-containing sample, does not induce agglutination. Therefore, when the CRP is to be quantitatively measured using the above-mentioned known monoclonal antibodies, it is necessary to use a sandwich assay or the like utilizing both monoclonal antibodies.

DISCLOSURE OF THE INVENTION

The present inventors, as a result of investigations aimed at inducing an agglutination of the CRP using only one monoclonal antibody, found novel monoclonal antibodies which react with a portion of a disk-like subunit of the CRP different from the portions with which the known monoclonal antibodies react.

Accordingly, the present invention provides monoclonal antibodies which react with the side face of the C-reactive protein (CRP), i.e., monoclonal antibodies which react with the side face of a disk-like subunit of the C-reactive protein (CRP) (C-face in FIG. 1; sometimes simply designated "C-face").

The present invention also provides monoclonal antibodies capable of inducing agglutination with C-reactive protein (CRP) on the basis of an antigen-antibody reaction.

Moreover, the present invention relates to hybridoma cells characterized in that they are constructed by a cell fusion of mouse myeroma cell with spleen cell of a mouse immunized by C-reactive protein (CRP), and secret a monoclonal antibody reactive with the side face of C-reactive protein (CRP).

Still further, the present invention relates to an immunoassay method for C-reactive protein (CRP) in a serum, characterized by using a monoclonal antibody which specifically reacts with the side face of C-reactive protein (CRP).

BEST MODE OF CARRYING OUT THE INVENTION

Figure 1:
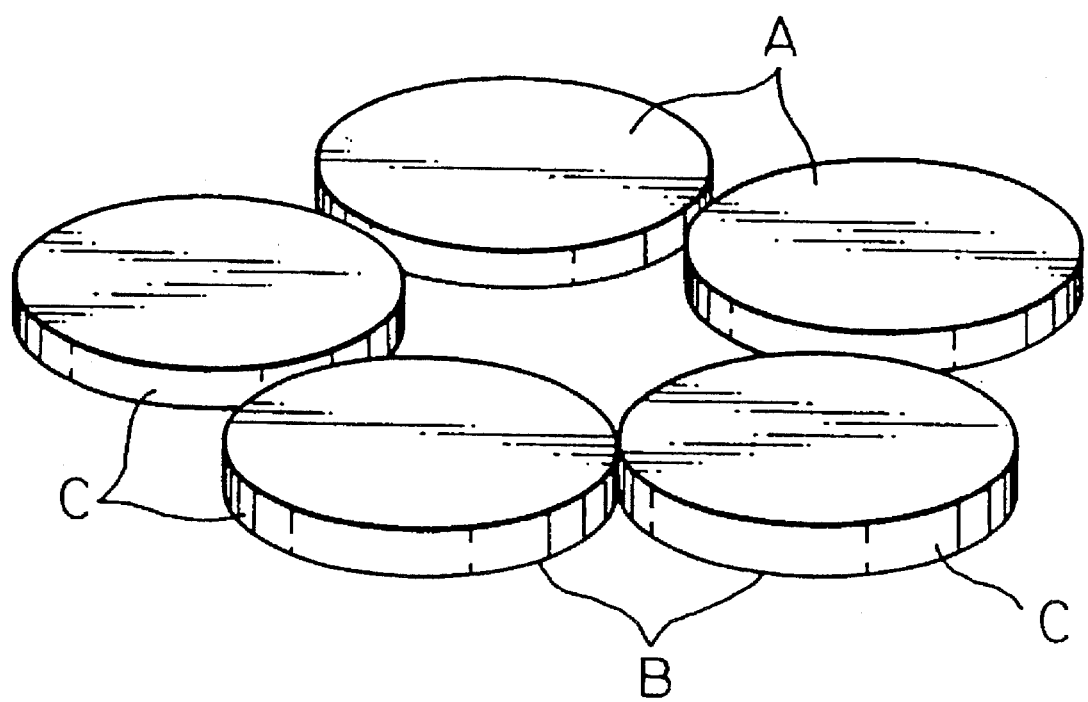
FIG. 1 schematically explains a structure of C-reactive protein (CRP)

Monoclonal antibodies according to the present invention, which are monoclonal antibodies to the CRP, can be produced by culturing a novel mouse-hybridoma cells in vitro (for example, in a culture medium) or in vivo (for example, peritoneally in mice).

Mouse-hybridoma cells used herein are generally prepared by fusing a mouse myeloma cell with a spleen cell of a mouse immunized with CRP, according to the Kohler and Milsteins method (see, Nature, Vol. 256, p 495, 1975).

As a medium for culturing the above-mentioned hybridoma cells, any medium suitable for culturing hybridoma cells can be used, but preferably Dulbecco's modified Eeagle's medium (abbreviated thereinafter as DME) containing fetal bovine serum, L-glutamine, L-pyruvate and antibiotics (penicillin G and streptomycin) is used.

The culturing of the above-mentioned hybridoma cells is carried out, for example, in a 5% $CO_2$ concentration at 37° C. for about 3 days in the case of an in vitro culture, or, for example, peritoneally in a mouse for about 14 days in the case of an in vivo culture.

For an isolation and purification of a monoclonal antibody from a cultured broth or the ascites of mouse thus-prepared, any process generally used for the isolation and purification of a protein can be used. Such processes include salting out with ammonium sulfate, ion exchange chromatography, molecular sieve column chromatography using a molecular sieve gel, affinity column chromatography using protein A-bounded polysaccharide, dialysis, and lyophilization and the like.

The anti-CRP monoclonal antibody thus obtained has an ability to specifically react with only CRP, without reacting with other plasma proteins. In addition, the anti-CRP monoclonal antibodies according to the present invention specifically react with only the side face (C-face) but do not react with the circular upper face (A-face) or the circular lower face (B-face), of a disk-like submit. Moreover, since the anti-CRP monoclonal antibodies, when immobilized on an insoluble carrier, can induce agglutination with CRP, they are useful as an immunoassay reagent for a quantitative determination of CRP. For example, a CRP quantitative determination by agglutination uses only one anti-CRP monoclonal antibody of the present invention, which is bonded to a conventional insoluble carrier (for example, a latex such as polystylene latex particles) by a known chemical bounding method (using as a cross-linking agent, carbodiimide, glutaraldehyde or the like) or physical adsorption to form a complex. A known amount of the anti-CRP monoclonal antibody-bonded insoluble carrier complex and a predetermined amount of an aqueous sample (for example, serum, plasma, or urine) containing an unknown amount of CRP are brought into contact in a reaction cell on a slide plate or in an appropriate reaction container, and from an amount of agglutination thus formed, the CRP concentration can be quantitatively determined. For example, an agglutination reaction is determined visually using a slide plate, or spectro-photometrically at a particular wave length using a reaction cell.

Moreover, the present anti-CRP monoclonal antibody can be used in combination with another monoclonal antibody (for example, an monoclonal antibody specifically reacting with the circular upper face or circular lower face of a disk-like subunit) to carry out a quantitative immunoassay for various CRP-containing aqueous samples.

EXAMPLE

Next, the present invention will be further illustrated by, but is no means limited to, the following examples.

EXAMPLE 1

(a) Preparation of immunized spleen cells

A CRP immunogen solution (PeL-Freez, US; A280 nm=0.1) was mixed with an equal amount of Freund's complete adjuvant to form an emulsion, and 200 μl of this mixture was intraperitoneally administered to a mouse for immunization (the first immunization). After 30 days from the first immunization, 200 μl of the same mixture was intraperitoneally administered to the mouse (the second immunization). After 21 days from the second immunization, a CRP immunogen solution (A280 mm=0.1) was diluted with an equal amount of physiological saline, and 200 μl of the diluted solution was intraveneously administered to said mouse (the last immunization). After 3 days from the last immunization, the spleen was aseptically removed from the mouse, to be used in the subsequent cell fusion step.

(b) Cell fusion

The spleen aseptically removed as described above was put into a petri dish containing 5 ml of DME medium supplemented with 15% fetal bovine serum. Next, the spleen was perfused with about 15 ml of DME supplemented with a 15% fetal bovine serum to wash out spleen cells, and the spleen cell suspension was passed through a nylon mesh. The spleen cell suspension was then collected in a 50 ml centrifugation tube, and centrifuged at 500× g for 10 minutes. The cell pellet thus obtained was suspended in 4 ml of a hemolyzing solution (155 mM $NH_4Cl$, 10 mM $KHCO_3$, 1 mM $Na_2EDTA$, pH 7.0). Erythrocytes in the suspension were lyzed by allowing to put at 0° C. for 5 minutes. After adding 10 ml of DME medium supplemented with 15% fetal bovine serum, the mixture was centrifuged, a resulting cell pellet was washed with DME medium by centrifugation, and viable spleen cells were counted.

On the other hand, $1\times10^8$ of the aboveprepared spleen cells were added to $2\times10^7$ of previously cultured mouse myeloma SP 2/0-Ag 14 cells (Rikagaku Kenkyu Sho, Gene Bank), and were thoroughly mixed in a DME medium and centrifuged (500× g, for 10 minutes). The supernatant was aspirated, the pellet was well slackened, 0.5 ml of 40% polyethylene glycol 4000 solution (kept at 38° C.) was dropwise added thereon, and the centrifugation tube was manually and gently rotated for a minute, to mix the ethylene glycol solution and the cell pellet. Next, 1 ml per 30 seconds of DME medium kept at 38° C. was added thereon, and the tube was manually and gently rotated. After repeating this procedure 10 times, 20 ml of a DME medium containing 15% fetal bovine serum was put thereon, and the mixture was centrifuged at 500× g for 10 minutes. After eliminating the supernatant, the cell pellet was washed two times with a HAT medium (prepared by adding $4\times10^{-7}M$ aminopterin, $1.6\times10^{-5}M$ thymidine and $1\times10^{-4}M$ hypoxanthine to DME medium) supplemented with 15% fetal bovine serum by centrifugation, and suspended in 40 ml of the above-mentioned HAT medium. Then, 200 μl of this cell suspension was distributed to each well of a 96-well cell culture plate, and culturing was started at 37° C. in a carbon dioxide incubator containing 5% carbon dioxide. During the culturing, at an interval of 2 to 3 days, about 100 μl of the medium was eliminated from each well and about 100 μl of fresh HAT medium added thereon, to select hybridoma growing in the HAT medium. Starting from the eighth day, the medium was exchanged with HT medium (prepared by adding $1.6\times10^{-5}M$ thymidine and $1\times10^{-4}M$ hypoxanthine to DME medium) supplemented with 15% fetal bovine serum while monitoring the growth of hybridoma, and on the tenth day the hybridoma were screened for CRP productivity by an ELISA method as described below.

(c) Establishment of hybridoma

The presence or absence of an antibody in a hybridoma culture supernatant was determined by the ELISA method. First, 50 μl of a diluted CRP immunogen solution (A280 nm=0.05, diluted with physiological saline) was distributed to each well of a 96-well ELISA plate (Immulon II, Nippon Dynatech K.K.), and the plate was allowed to stand at 25° C. for 2 hours. Next, after washing three times with a 0.05% Tween (trademark) 20-physiological saline, 50 μl of a culture supernatant was added to each well and a reaction was allowed at 25° C. for one hour.

Next, 50 μl of peroxidase-linked mouse antibody (DAKO, Denmark) diluted 200 fold with a Tween 20-physiological saline was added to each well. After completing the reaction, each well was washed three times with a 0.05% Tween 20-physiological saline, and to each well was added 250 μl of a solution containing 0.5 mM aminoantipyrine, 10 mM phenol and 0.005% hydrogen peroxide, and after a reaction at 25° C. for 30 minutes, the absorbance at 490 nm was measured for each well. As a result, 4 among 192 wells indicated the production of an antibody. Hybridoma cells in the 4 wells were transferred to 24-well plates, and cultured in an HT medium containing a 15% fetal bovine serum for 4 to 5 days, and after a further confirmation of the production of the anti-CRP antibody by the ELISA method, were cloned by a limiting dilution method. In the limiting dilution method, 100 μl of a cell suspension diluted with HT medium to 5 hybridoma cells/ml was distributed to each well of a 96-well plate, in which well $2\times10^4$ peritoneal cells of normal BALB/C mouse had been distributed. Ten days later, hybridoma clones were screened for the production of an anti-CRP specific antibody, by the ELISA method, and as a result, 20 to 40 antibody-producing clones were obtained from each hybridoma. Among these clones, those clones which grew well, had a high ability to secret an antibody and were stable, were selected and re-cloned as described above to establish an anti-CRP specific antibody-producing hybridoma CRP-1, CRP-2, CRP-3 and CRP-4. These hybridoma were deposited with the Fermentation Research Institute Agency of Industrial Science and Technology (FRI) 1–3 Higashi 1-chome, tsukuba-shi, Ibaraki-ken, Japan, on Apr. 13, 1989, and have the following accession numbers.

| Hybridoma | Accession number |
|---|---|
| CRP-1 | FERM BP-2873 |
| CRP-2 | FERM BP-2874 |
| CRP-3 | FERM BP-2875 |
| CRP-4 | FERM BP-2875 |

EXAMPLE 2

Production of monoclonal antibody (a) In vitro process

The hybridoma CRP-1, CRP-2, CRP-3 and CRP-4 were separately cultured in DME medium containing a 15% fetal bovine serum at 37° C. in a 5% carbon dioxide atmosphere for 72 to 96 hours. The culture was centrifuged (at 1000× g, for 10 minutes), and to the supernatant was gradually added a solid ammonium sulfate, to make a final concentration of the ammonium sulfate 50%. The mixture was stirred under ice-cooling for 30 minutes, allowed to stand for 60 minutes, centrifuged (at 10,000× g, for 10 minutes), a resulting precipitate was dissolved in a small amount of a 10 mM phosphate buffer (pH 8.0), and the solution was dialyzed against a 1000 times volume of 10 mM phosphate buffer. The dialyzate was filled in a DEAE-cellulose column equilibrated with 10 mM phosphate buffer, and a monoclonal antibody was eluted with a concentration gradient of between a 10 mM phosphate buffer (pH 8.0) and a 10 mM phosphate buffer (pH 8.0) containing 0.2M NaCl. The eluted monoclonal antibody was concentrated by ultrafiltration, and dialyzed against a 0.1M phosphate buffer (pH 8.0). To eliminate the bovine serum IgG, the dialyzate was passed through an anti-bovine serum goat IgG-Sepharose 4B column. Next, the filtrate was filled in a protein A-Sepharose 4B column equilibriated with a 0.1M phosphate buffer (pH 8.0), and the column was subjected to elution with a buffer having a pH of 3.5 to obtain a solution of a purified anti-CRP specific antibody CRP-1 (this also applies to the CRP-2, CRP-3 and CRP-4).

(b) In vivo process

First, 0.5 ml of pristane (2,6,10,14-tetramethylpentadecane) was intraperitoneally administered to BALB/C mice 10 to 12 weeks old, and then hybridoma CRP-1, CRP-2, CRP-3 or CRP-4 cells grown in vitro were inoculated to the mice in $2 \times 10^6$ cells per mouse.

For each hybridoma about 10 to 15 ml per mouse of the ascites was obtained. A concentration of antibody therein was 2 to 10 mg/ml. The monoclonal antibody in the ascites was purified by the same procedure as described above for the in vitro-purification (except that the anti-bovine serum goat IgG-Sepharose 4B column step was omitted).

EXAMPLE 3

Identification of immunoglobulin class and specificity of monoclonal antibody The immunoglobulin class and specificity of the anti-CRP specific monoclonal antibodies CRP-1, CRP-2, CRP-3 and CRP-4 were determined by the Ouchterlony diffusion method and an enzyme immunoassay, respectively. The results are shown in Table 1.

TABLE 1

| Monoclonal Antibody | Immunoglobulin class |
|---|---|
| CRP-1 | $IgG_1$ |
| CRP-2 | $IgG_1$ |
| CRP-3 | $IgG_1$ |
| CRP-4 | $IgG_1$ |

EXAMPLE 4

Binding of antibody to insoluble carrier (latex) and confirmation of reaction site First, 2 ml of a latex solution (2%, Dow Chemical: diameter 0.482 μm) and 2 ml of a 2.0 mmg/ml CRP-1 antibody aqueous solution were mixed and the mixture was stirred for about one hour. After centrifugation (at 20,000× g for 10 minutes), precipitate was suspended in a 0.1% BSA solution, and the mixture stirred for about one hour. The mixture was again centrifuged (at 20,000× g, for 10 minutes), the resulting precipitate was suspended in water, and the suspension was stirred for about two hours. In this manner, a suspension containing a CRP-1 antibody-latex complex was obtained. Similarly, suspensions containing a complex were obtained using the CRP-2 antibody, CRP-3 antibody and CRP-4 antibody, respectively.

On the other hand, a monoclonal antibody specifically reacting with the A-face of CRP but not reacting with the B-face (A-antibody), and a monoclonal antibody specifically reacting with the B-face of CRP but not reacting with the A-face (B-antibody) were prepared according to the Journal of Immunology Vol. 131, pp 2411–2415, and suspensions containing a complex were prepared as described above.

Next, 30 μl of the complex-containing suspension and 30 μl of a 25 μl/ml CRP solution were mixed on a slide glass, and the agglutination was visually observed. As a result, although an agglutination was not observed for the A-antibody and B-antibody, an agglutination was confirmed for CRP-1, CRP-2, CRP-3 and CRP-4 of the present invention. Accordingly, it is clear that the present CRP-1, 2, 3 and 4 antibodies are clearly different from a conventional antibody capable of specifically reacting with only the A-face and a antibody capable of specifically reacting with only the B-face.

Accordingly, a solution containing 20 μg/ml CRP masked at the A-face of the CRP with a corresponding antibody, and a solution containing 20 μg/ml CRP masked at the B-face of the CRP with a corresponding antibody were prepared, to 30 μl of the solution was added 30 μl of the above-mentioned antibody complex-containing suspension, and they were mixed on a slide glass. As a result, it was confirmed that the present CRP-1, 2, 3 and 4 antibodies induced the agglutination. This suggests that a specific reaction site of the present antibody is a site different from the A-face and B-face of CRP, and that since the present antibodies provide an agglutination by their reaction with CRP, the present antibodies specifically react with the side face of CRP.

EXAMPLE 5

Quantitative assay by slide agglutination reaction

First, 30 μl of antibody latex complex suspension and 30 μl of an aqueous solutions containing different concentrations of CRP were mixed on a slide, and after shaking the slide for three minutes, an agglutination profile was visually observed. The results are shown in Table 2.

TABLE 2

| Antibody | CRP Concentration (μg/ml) | | | | | | | | | | | |
|---|---|---|---|---|---|---|---|---|---|---|---|---|
| | 256 | 128 | 64 | 32 | 16 | 8 | 4 | 2 | 1 | 0.5 | 0.25 | 0.125 | 0.063 |
| CRP-1 | + | + | + | + | + | + | + | + | + | + | + | + | − |
| CRP-2 | + | + | + | + | + | + | − | − | − | − | − | − | − |
| CRP-3 | + | + | + | + | + | − | − | − | − | − | − | − | − |
| CRP-4 | + | + | + | + | + | + | + | + | + | − | − | − | − |

In Table 2, the symbols + and − denote the presence and absence of agglutination, respectively.

EXAMPLE 6

Assay by spectrophotometry

Figure 2:
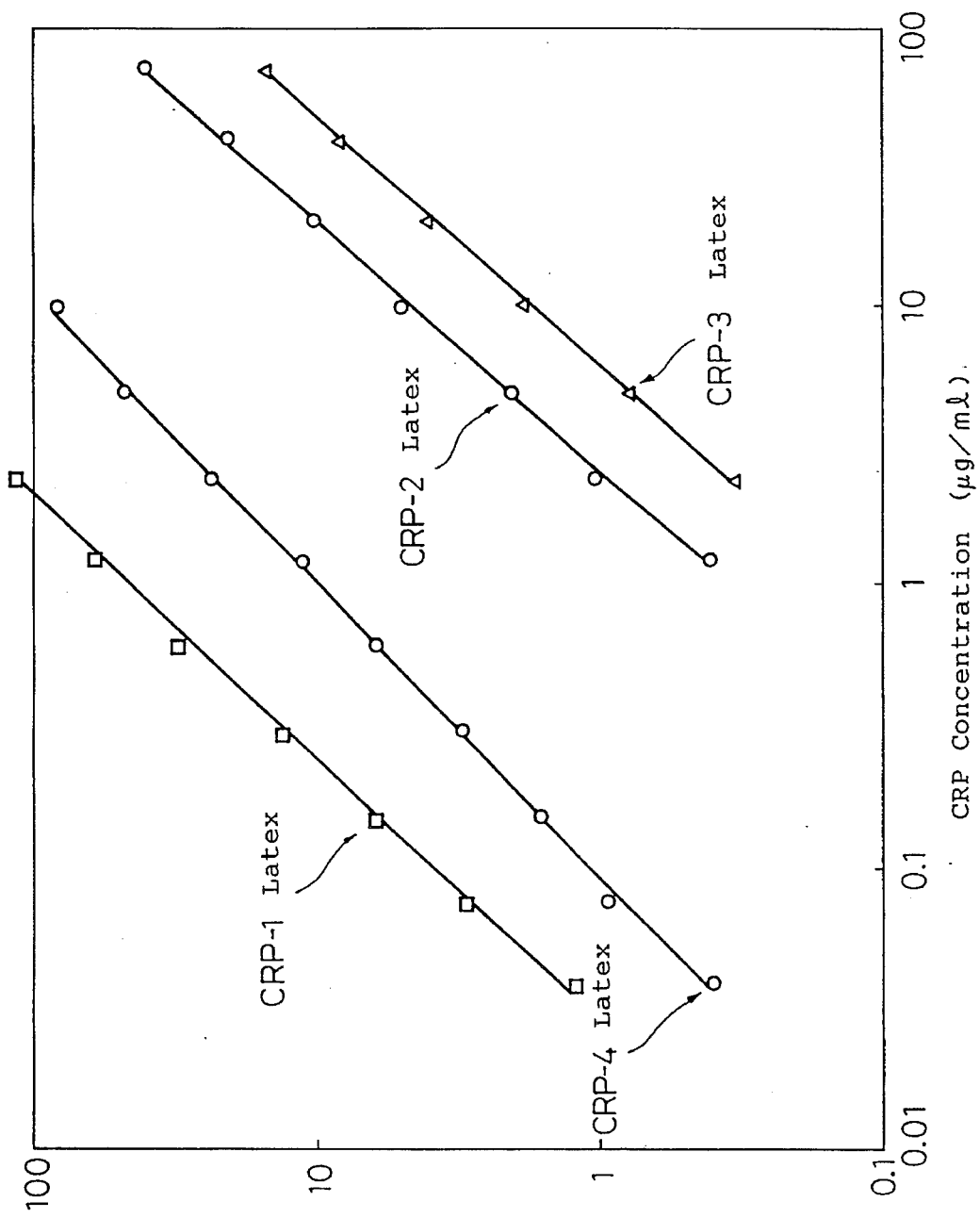
FIG. 2 is a graph showing the relationship between the agglutination rate and the CRP concentration.

Latex (particle diameter 0.482 μm, Dow, Germany) coated with one of the monoclonal antibodies CRP-1, CRP-2, CRP-3 and CRP-4 prepared in Example 4 was used to test the human CRP concentration dependency of the agglutination rate, on a automatic analyzer (note: general name LPIAL-1; Mitsubishi Chemicals). As the human CRP, a product commercially available from PeL-Freez (US) was used, and 12 aqueous solutions containing human CRP at a concentration of 0.04 μg/ml to 80 μg/ml were prepared. The results are shown in FIG. 2. As seen from FIG. 2, each of the four later shows a CRP concentration-dependent agglutination rate (V value: change in transparency per time).

INDUSTRIAL APPLICABILITY

The present monoclonal antibodies are useful for measuring an amount of CRP in various samples.

Reference to microorganisms deposited under Rule 13-2, and depository authority: Fermentation Research Institute Agency of Industrial Science and Technology, the Ministry of International Trade and Industry Address: 1-3 Higashi 1-chome, Tsukuba-shi, Ibaraki-ken, Japan

| Deposition number and deposition date | |
|---|---|
| 1. FERM BP-2873 | April 13, 1989 |
| 2. FERM BP-2874 | April 13, 1989 |
| 3. FERM BP-2875 | April 13, 1989 |
| 4. FERM BP-2986 | April 13, 1989 |

We claim:

1. A monoclonal antibody specific for C-reactive protein wherein the monoclonal antibody can agglutinate latex particles to which said monoclonal antibody has been immobilized upon binding of said monoclonal antibody to C-reactive protein, wherein the monoclonal antibody is selected from the group consisting of monoclonal antibody CRP-1 produced by hybridoma cell line CRP-1 (FERM BP-2873), monoclonal antibody CRP-2 produced by hybridoma cell line CRP-2 (FERM BP-2874), monoclonal antibody CRP-3 produced by hybridoma cell line CRP-3 (FERM BP-2875), and monoclonal antibody CRP-4 produced by hybridoma cell line CRP-4 (FERM BP-2876).

2. A hybridoma cell line capable of producing a monoclonal antibody specific for C-reactive protein where the monoclonal antibody can agglutinate latex particles to which said monoclonal antibody has been immobilized upon binding of said monoclonal antibody to C-reactive protein wherein the cell line is selected from the group consisting of hybridoma cell line CRP-1 (FERM BP-2873, hybridoma cell line CRP-2 (FERM BP-2874, hybridoma cell line CRP-3 (FERM BP-2875, and hybridoma cell line CRP-4 (FERM BP-2876).

3. An immunoassay method for C-reactive the detection of protein using a monoclonal antibody specific for to C-reactive protein wherein the monoclonal antibody can agglutinate latex particles on which said monoclonal antibody has been immobilized upon binding of said monoclonal antibody to C-reactive protein which comprises the steps of (1) bringing the monoclonal antibody in contact with a sample under conditions which allow binding of the monoclonal antibody to C-reactive protein, and (2) detecting the immunospecific binding, wherein the monoclonal antibody is selected from the group consisting of monoclonal antibody CRP-1 produced by hybridoma cell line CRP-1 (FERM BP-2873), monoclonal antibody CRP-2 produced by hybridoma cell line CRP-2 (FERM BP-2874), monoclonal antibody CRP-3 produced by hybridoma cell line CRP-3 (FERM BP-2875), and monoclonal antibody CRP-4 produced by hybridoma cell line CRP-4 (FERM BP-2876).

4. An immunoassay method the detection of C-reactive protein according to claim 3, wherein the immunoassay is a latex agglutination assay.

* * * * *